United States Patent [19]

Bryans

[11] 4,083,958
[45] Apr. 11, 1978

[54] INACTIVATED EQUINE RHINOPNEUMONITIS VIRUS VACCINE AND USE THEREOF

[75] Inventor: John T. Bryans, Lexington, Ky.

[73] Assignee: The University of Kentucky Research Foundation, Lexington, Ky.

[21] Appl. No.: 722,817

[22] Filed: Sep. 13, 1976

[51] Int. Cl.$^2$ ............................................. A61K 39/12
[52] U.S. Cl. ..................................... 424/89; 195/1.1; 195/1.3; 195/1.7
[58] Field of Search .................................. 195/1.1–1.8; 424/89

[56] References Cited

PUBLICATIONS

Vet. Bull. 46 (1976) #633–#637, #1305–#1306, #2452 #2453.
Vet. Bull. 45 (1975) #951, #1633–#1635, #4957 #4958.
Vet. Bull. 44 (1974) #1546–#1547, #5445.
Vet. Bull. 42 (1973) #2453, #3834, #4568, #6262, #6850.

Primary Examiner—Shep K. Rose
Attorney, Agent, or Firm—Birch, Stewart, Kolasch and Birch

[57] ABSTRACT

An inactivated viral vaccine for protecting horses against disease caused by equine rhinopneumonitis virus is prepared by propagating an equine rhinopneumonitis virus in a susceptible, cloned, diploid equine cell line, harvesting the resulting virus in a serum-free medium, inactivating the virus and neutralizing the inactivating agent, concentrating the virus, and adding an immunological adjuvant thereto. A vaccination program to protect horses against the equine rhinopneumonitis virus is also disclosed.

9 Claims, No Drawings

INACTIVATED EQUINE RHINOPNEUMONITIS VIRUS VACCINE AND USE THEREOF

This invention relates to the development of a preventive immunization method for protecting pregnant mares against the abortigenic effect of equine rhinopneumonitis virus (equine herpesvirus I) infection and of protecting young horses against disease caused by their infection by the same virus and to the process of preparation of the potent vaccine.

The equine rhinopneumonitis virus (ERV), a typical member of the Herpesvirus group, infects the respiratory mucosa and subjacent or associated lymphoreticular organs leading to development of a cell-associated viremic state which may lead to abortigenic infection of the fetus in pregnant mares. The economic losses consequent to disease produced by this infection in young horses result from inability or impaired ability to perform in competition. The economic losses resulting from infection of pregnant mares are due to abortion. The disease occurs in enzootic form but may occur in epizootic form resulting in fetal or neonatal loss of greater than 50 percent of expected foal crop production in individual bands of mares.

Hitherto, it has not been possible to prevent such loss without risk of vaccine induced abortic infection in which living virus vaccines are administered either intranasally or parenterally. Infectious (living-attenuated) vaccines may not be used except in early or mid-gestation, these periods being the least critical during which protection is required.

It is known that certain properly constituted, chemically inactivated, non-infectious viral vaccines will protect mammals against disease caused by specific viruses. There is, however, no teaching in the art, or no example in the scientific literature, that an inactivated viral vaccine will protect mares against abortigenic infection by equine rhinopneumonitis herpesvirus.

The present invention provides an injectable vaccination program, timed to coincide with the most susceptible period of gestation of the equine fetus, as well as an immunogenically potent vaccine for immunizing horses against equine viral rhinopneumonitis and a process for preparing the vaccine wherein an antigenically typical and virulent equine rhinopneumonitis virus, propagated in a physiologically homogeneous cell culture derived as the recent progeny of a single cell cloned from a cell culture derived from the skin of a normal equine fetus, is chemically inactivated, concentrated by ultrafiltration and mixed for enhancement of immunogenic potency for injection with an oil based immunological adjuvant.

More particularly, the invention provides an intramuscular vaccination protocol for protection of pregnant mares against abortion caused by equine rhinopneumonitis viral infection which consists in vaccinating pregnant mares by injection in the 5th month of pregnancy, in the 7th month and in the 9th month of pregnancy, and of immunizing non-pregnant yearlings by a series of two injections in September and an annual single injection vaccination until such female yearlings reach breeding age and become pregnant with a vaccine prepared by:

(A) Preparing from the dermis of a normal equine fetus, removed aseptically from a pregnant normal mare, a cell culture which by karyotypic analysis is shown to be a diploid male or female idiogram without any abnormal chromosome markers and containing the normal modal chromosome number for *Equus caballus* (64), (B) Preparing from this cell culture, single cell cloned diploid cell lines which by karyotypic analysis reveal a stable emploidy and showing, by virus culture, electron microscopy, bacteriological culture and uridine-uracil ratio, that such cell lines are free of adventitious viruses, bacterial or mycoplasma, (C) Determining by inoculation of horses and preparation of antiserums in rabbits against the cell culture that the cell culture contains no equine red blood cell antigens, (D) Inoculating such cell lines with a multiplicity of infections shown to produce maximum infectious virus particle yields of a stable macroplaque strain of an antigenically typical equine rhinopneumonitis virus and causing the virus to be released into a serum-free medium, and (E) Harvesting such serum-free virus containing material from infected cell culture, removing cell culture debris by centrifugation, chemically inactivating infectivity of the virus with such chemicals as formalin, beta-propiolactone or acetylethylenimine, neutralizing any residual chemical, concentrating the virus by ultrafiltration, adding a stabilizing agent, adding a preservative, ascertaining that no residual infectious virus is present and mixing the virus with an oil based immunologic adjuvant. Said virus before addition of adjuvant must meet the following criteria for inactivation and integrity of structure:

(a) Virus is pelleted from a 100 ml sample of the completely mixed but unconcentrated inactivated virus base pool by centrifugation at 25,000 rpm for 1 hour. The pellet is resuspended in a few ml of serum-free balanced salt solution and two confluent monolayers of susceptible cell cultures are inoculated, each with half of the concentrated inactivated virus. If no viral cytopathic effect occurs after an incubation period of 7 days, each inoculated culture is harvested and transferred to a second set of two cell cultures. If no viral cytopathic effect occurs in these cultures after 7 days of incubation the virus is judged to be non-infectious.

(b) A virus pellet from the concentrated inactivated virus base pool is examined by ultra thin section electron microscopy to determine whether the inactivated virus particles are enveloped. Because potency of vaccine requires enveloped virions, the majority of the virions must be so constituted.

The inactivated virus must meet the following criteria for immunogenic potency:

The vaccine virus without adjuvant is diluted so as to decrease, in serial fashion, the number of inactivated virions in the suspension. The dilutions are extended to produce complete extinction of protective effect. A portion of each diluted virus suspension is mixed and emulsified with an equal amount of oil based adjuvant. Four Syrian hamsters (*Cricetus auratus*) are injected intramuscularly with 0.2 ml of each dilution of adjuvanted virus dilution. At the same time, four hamsters are mock vaccinated using a 0.2 ml intramuscular injection composed of equal amounts of emulsified diluent and adjuvant. Three weeks later, the hamsters are all challenged by intraperitoneal injection of at least 1 million hamster median lethal doses of hamster virulent virus. The hamsters are individually housed for the purposes of the test and are observed for 7 days following challenge inoculation. The vaccine must protect hamsters vaccinated with a 1:1500 dilution of the base vaccine virus suspension. The mock vaccinated hamsters must all die within 7 days, and a titration of the challenge virus in unvaccinated or mock vaccinated hamsters must show that the challenge virus contained at least 1 million hamster median lethal doses. The potency titration endpoint is the dilution of adjuvanted vaccine which protects 50 percent of vaccinated hamsters.

The invention further provides a process for manufacture of a vaccine characterized by the aforementioned protocols and the vaccine itself as a method for protecting horses against disease caused by the equine rhinopneumonitis virus.

As the virus, antigenically typical equine rhinopneumonitis virus, the A-183 strain, is used. The A-183 strain is immunogenically the same as strains of equine rhinopneumonitis virus recovered from diseased horses in several countries of the world, specifically Germany, Sweden, Switzerland, France, Great Britain, Ireland, Japan, Australia, South Africa, Argentina, Brazil and the United States. The virus may be recovered by inoculation of susceptible cell cultures, from the nasopharynx and/or blood of horses with respiratory disease, from the nasopharynx and/or blood of infected pregnant mares and from the organs of fetuses aborted by infected mares.

Although the virus may be cultured by multiplication in cell cultures derived from organs of many mammalian species, for the purposes of this invention, the virus is cultured from the lung tissue of an infected aborted fetus by inoculation of a cloned, diploid cell culture prepared from a cell culture derived from the dermis of a normal equine fetus.

The parent cell line is derived from the normal dermal and subcutaneous connective tissues of a normal 10 to 11-month-old equine fetus. Monolayer cultures are prepared from the excised and trypsin dispersed fetal connective tissue; cells from early 5th to 7th passage are stored at −90° Centigrade. To obtain a physiologically homogeneous cell population in culture as the progeny of a single cell, cloned lines of cells are initiated from the early subculture generations by single cell isolation techniques. The growth characteristics of cloned cell lines are determined by such techniques as plaquing efficiency, generation time and cell viability.

Karyotypic analysis of vinblastine treated cloned cell lines at the passage level selected for production of vaccine virus reveal diploid male or female idiograms without demonstrable chromosome markers. The cell lines are shown to be free of mycoplasma and adventitious viruses. Such cell lines have been shown to be capable of propagating all strains of equine rhinopneumonitis virus, equine cytomegalovirus, equine coital exanthema virus, Herpes simplex virus, infectious bovine rhinotracheitis virus, Venezuelan equine encephalomyelitis virus, equine adenovirus, and equine arteritis virus. The cell lines can be shown to be free of equine infectious anemia virus by inoculation of susceptible horses.

When rabbits are immunized with the cell lines, they produce no antibodies reactive against known equine red blood cell antigens. Inoculation of normal horses with the cell lines produces no adverse effect.

For virus vaccine production, cell cultures are prepared as confluent monolayers in glass or plastic roller bottles. The cells are grown in medium consisting of Eagle's Minimal Essential Ingredient with Hank's salts, L-glutamine, non-essential amino acids, 0.6 grams per liter of bicarbonate, and 10 percent calf serum or fetal calf serum. Virus growth curves illustrate conditions of incubation yielding maximum yields. Studies of virus propagation determined that virus release into calf serum-free medium is accomplished by removing serum-containing medium before virus release occurs, thereby obtaining virus yields free of foreign serum protein and hence removing extraneous antigenic material from the vaccine.

Infectious virus yields from cultures so prepared average 6.0 to 7.0 $\times$ $10^6$ plaque forming units per milliliter of cell free virions.

The virus suspensions harvested from such cell cultures are centrifuged to remove extraneous cell debris and the supernatant solutions are pooled to constitute a production lot. The virus is chemically inactivated, the residual inactivating chemical is neutralized and the virus is tested for inactivation by the test described above. The inactivated virus pool is then concentrated to increase antigenic potency by ultrafiltration using a membrane with an exclusion limit of molecular weight 5000. A sample of the concentrated vaccine is pelleted by centrifugation and the virus pellet is examined by thin layer electron microscopy to determine the presence of enveloped virions. The vaccine virus is tested for bacterial contamination. A stabilizer and a preservative such as thiomerosal are added.

The inactivated vaccine virus is emulsified with an equal amount of oil based adjuvant and dispensed aseptically into suitable containers.

The following example illustrates the invention but is not intended to limit it thereto:

EXAMPLE I

Of a group of 21 pregnant mares, 11 were vaccinated with adjuvanted, inactivated virus vaccine with a hamster immunogenic potency of 1:1600. There was no untoward local or generalized reaction to injection of the vaccine. An immune response evident by post-vaccinal increase in antibody and by other parameters applicable to in-vitro measurement of such response was noted for each mare. Sixty days after vaccination the vaccinated mares and the 10 unvaccinated mares were exposed to virulent rhinopneumonitis virus by the intranasal route which is the natural route of transmission of the virus. Six of the unvaccinated mares aborted rhinopenumonitis virus infected fetuses, four delivered normal foals. All of the vaccinated mares delivered normal foals.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A vaccination method against disease caused by equine rhinopneumonitis virus in horses which comprises (a) vaccinating young female horses at any age past the time they reach their sixth month of age and revaccinating them at appropriate intervals until the females reach breeding age and become pregnant and (b) vaccinating the pregnant mares during their pregnancy and during subsequent pregnancies with an adjuvanted, inactivated vaccine prepared by:

propagating a virulent, immunogenically typical equine rhinopneumonitis virus in a susceptible, cloned, diploid equine cell line that contains no equine blood cell antigens, and causing the virus to be released into a serum-free medium;

harvesting virus from the cell culture, inactivating the virus, neutralizing the inactivating agent, concentrating the virus and adding an oil based immunological adjuvant thereto.

2. The vaccination method in accordance with claim 1, wherein said harvested material meets the following criteria for safety and potency:

(a) the virus is shown to be inactivated and non-infective by its lack of ability to infect susceptible cell cultures, and (b) the vaccine is shown to be immunogenically potent by protection of hamsters against one million hamster median lethal doses of hamster virulent rhinopneumonitis virus.

3. The vaccination method in accordance with claim 1, wherein the young horses are revaccinated about 3 weeks after their first vaccination and then at yearly intervals thereafter until they reach breeding age.

4. The vaccination method in accordance with claim 3, wherein the pregnant mares are vaccinated at the fifth, seventh and ninth months of pregnancy.

5. The method of preparing a vaccine for parenteral vaccination of horses against disease caused by equine rhinopneumonitis virus which comprises:

propagating a virulent, immunogenically typical equine rhinopneumonitis virus in a susceptible equine, cloned, physiologically homogeneous, diploid cell line and multiplying the virus to obtain high yields of infectious virions;

harvesting the virus in a serum free medium;

completely inactivating the virions, neutralizing the inactivating agent, concentrating the virions by a method that maintains structural integrity and increases antigenic potency; and mixing the concentrated, inactivated virions with an oil based immunological adjuvant, said harvested and adjuvant mixed material meeting the following criteria for safety and potency;

(a) the virus is shown to be inactivated and non-infective by its lack of ability to infect susceptible cell cultures, and (b) the vaccine is shown to be immunogenically potent by protection of hamsters against one million hamster median lethal doses of hamster virulent rhinopneumonitis virus.

6. A vaccine for protection of horses against equine rhinopneumonitis prepared by the method of claim 5.

7. The method of protecting horses against equine rhinopneumonitis which comprises vaccinating said horses with a vaccine prepared by the method of claim 5.

8. The vaccination method in accordance with claim 1, wherein said rhinopneumonitis virus is obtained from an infected fetus.

9. The method of claim 5, wherein said rhinopneumonitis virus is obtained from an infected equine fetal lung.

* * * * *